United States Patent
Hietala

(10) Patent No.: US 8,220,311 B2
(45) Date of Patent: Jul. 17, 2012

(54) SYSTEM AND METHOD FOR MEASURING CONCENTRATION OF A PARAMAGNETIC GAS

(75) Inventor: Mika Harri Juhani Hietala, Helsinki (FI)

(73) Assignee: General Electric Company, Schenectady, NY (US)

( * ) Notice: Subject to any disclaimer, the term of this patent is extended or adjusted under 35 U.S.C. 154(b) by 474 days.

(21) Appl. No.: 12/630,431

(22) Filed: Dec. 3, 2009

(65) Prior Publication Data

US 2011/0132070 A1    Jun. 9, 2011

(51) Int. Cl.
*G01N 27/74*    (2006.01)
(52) U.S. Cl. ................... 73/25.02; 324/204
(58) Field of Classification Search ............ 73/25.02; 324/204
See application file for complete search history.

(56) References Cited

U.S. PATENT DOCUMENTS

| | | | |
|---|---|---|---|
| 4,403,186 A | 9/1983 | Kotani et al. | |
| 4,633,705 A | 1/1987 | Merilainen et al. | |
| 4,808,921 A * | 2/1989 | Christensen | 324/204 |
| 4,860,574 A | 8/1989 | Maeda et al. | |
| 6,263,722 B1 | 7/2001 | Fabinski et al. | |
| 6,520,001 B2 | 2/2003 | Dempster et al. | |
| 2007/0084265 A1 * | 4/2007 | Haveri | 73/25.02 |

FOREIGN PATENT DOCUMENTS

| | | |
|---|---|---|
| EP | 1775582 A1 | 4/2007 |
| GB | 2158949 A | 11/1985 |
| GB | 2191294 A | 12/1987 |
| WO | 9420846 A1 | 9/1994 |

OTHER PUBLICATIONS

Search Report from corresponding EP Application No. 10192740.8 dated Dec. 5, 2011.

* cited by examiner

*Primary Examiner* — Hezron E Williams
*Assistant Examiner* — Nathaniel Kolb

(57) ABSTRACT

In one embodiment, a device for measuring concentration of a paramagnetic gas is provided. The device comprises a measuring cell having a closed cavity therein, a reference gas conduit extending into the cavity for supplying a reference gas to the measuring cell, the reference gas comprising a predetermined concentration of the paramagnetic gas, a measurable gas conduit extending into the cavity for supplying a measurable gas to the measuring cell, the measurable gas comprising a measurable concentration of the paramagnetic gas, a first microphone differentially coupled to the measurable gas conduit and the reference gas conduit, and a second microphone located at a predetermined distance from the reference gas conduit.

19 Claims, 5 Drawing Sheets

SYSTEM AND METHOD FOR MEASURING CONCENTRATION OF A PARAMAGNETIC GAS

FIELD OF INVENTION

The invention generally relates to a device for measuring contents and proportions of gases in a gaseous mixture and more particularly to a device for determining concentration of a paramagnetic gas in a gas sample.

BACKGROUND OF THE INVENTION

Breath gases are measured in hospitals for several reasons and in several departments. Typical measured gases are one or several of the following gases: Carbon dioxide (CO2), Oxygen (O2), Nitrous oxide (N2O) and anesthetic gases (halothane, sevoflurane, desflurane, isoflurane and enflurane). Gases are measured either using sidestream technique (non-diverting) or mainstream technique (diverting). In the sidestream technique a gas sample is transferred through a sample line to a sensor, which causes a delay between breath and measurement. On the other hand, in the mainstream technique the gas sample is analyzed at the sampling site.

Variety of measurement techniques exist for measuring concentration of different gases. Paramagnetic analyzing technique is one of the side stream measurement techniques suitable for oxygen measurement. The paramagnetic measurement principle employs a paramagnetic sensor suitable for oxygen measurement as the oxygen has paramagnetic properties.

There are different kinds of paramagnetic oxygen sensors described in the prior art. However, one of the paramagnetic sensors comprises a reference flow, which is normal room air consisting of predetermined percentage of oxygen, and measurable flow of which oxygen concentration is to be analyzed. Both flow rates are approximately the same and they have the same pressure. The reference flow and the measurable flow are mixed in an air gap of a magnet having a strong magnetic AC-field. The AC magnetic field causes the oxygen molecules to move in a frequency that is double the magnet control frequency. This movement causes pressure variation, which can be measured for example with sensitive microphone(s). Because microphones are sensitive devices, they also sense mechanical and pneumatics interferences, which should be minimized.

One of the methods suggested in the prior art to measure the gas signal, uses a microphone connected between the reference flow and the measurable flow. The microphone measures the gas signal differentially and is well positioned to compensate the pneumatic interferences in normal situations but is sensitive to mechanical interferences.

Another method suggested in the prior art uses two microphones, one microphone for measuring the gas signal from the reference flow and another microphone for measuring the gas signal from the measurable flow. The two microphones used herein are connected using a single-end. The signals obtained from these two microphones are subtracted using suitable electronics.

The mechanical and the pneumatics interferences can be subtracted when the microphones are connected in the way described in the latter method. This helps in eliminating the mechanical and pneumatics interferences as the two microphones sense the pneumatics and mechanical interferences in the same way. However, in practice the mechanical and pneumatics interferences can't be eliminated altogether as there exists some sort of differences such as phase difference between the signals, as the signals pass through the microphones and their associated circuitry. Another limitation associated with the above-described methods is the difficulty associated with separating the gas signal from the mechanical and pneumatic interferences.

Hence, there exists a need to provide an accurate and reliable method for measuring oxygen concentration using a paramagnetic gas sensor.

BRIEF DESCRIPTION OF THE INVENTION

The above-mentioned shortcomings, disadvantages and problems are addressed herein which will be understood by reading and understanding the following specification.

In one embodiment, a device for measuring concentration of a paramagnetic gas is provided. The device comprises a measuring cell having a closed cavity therein, a measurable gas conduit extending into the cavity for supplying a measurable gas to the measuring cell, a reference gas conduit extending into the cavity for supplying a reference gas to the measuring cell, a first microphone differently coupled to the measurable gas conduit and the reference gas conduit and a second microphone located at a predetermined distance from the reference gas conduit.

In another embodiment, a paramagnetic gas analyzer comprising a measuring cell containing a reference gas and a measurable gas is provided. The measurable gas comprises a measurable concentration of the paramagnetic gas and the reference gas comprises a predetermined concentration of the paramagnetic gas. The paramagnetic gas analyzer further comprises a reference gas conduit for supplying the reference gas to the measuring cell and a measurable gas conduit for supplying the measurable gas to the measuring cell. The paramagnetic gas analyzer further comprises a first microphone differentially coupled to the reference gas conduit and the measurable gas conduit, a second microphone located at a predetermined distance from the reference gas conduit and a signal processing unit coupled to the first microphone and the second microphone. The first microphone is configured for providing a first signal, the first signal comprising at least one mechanical signal and at least one gas signal. The second microphone is configured for providing a second signal, the second signal comprising at least one mechanical signal. The signal processing unit is configured for measuring paramagnetic gas concentration of the measurable gas based on the signals from the first microphone and the second microphone.

In yet another embodiment, a method of measuring concentration of a paramagnetic gas is provided. The method comprises steps of coupling a first microphone differentially to a reference gas conduit and a measurable gas conduit, the reference gas conduit configured for supplying a reference gas and the measurable gas conduit configured for supplying a measurable gas, the reference gas comprising a predetermined concentration of the paramagnetic gas and the measurable gas comprising a measurable concentration of the paramagnetic gas, locating a second microphone at a predetermined distance from the reference gas conduit, coupling a signal processing unit to the first microphone and the second microphone, obtaining a first signal from the first microphone, the first signal comprising at least one mechanical signal and at least one gas signal, obtaining a second signal from the second microphone, the second signal comprising at least one mechanical signal, processing the signals obtained from the first microphone and the second microphone and measuring concentration of the paramagnetic gas based on the processed signals.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

Figure 1:
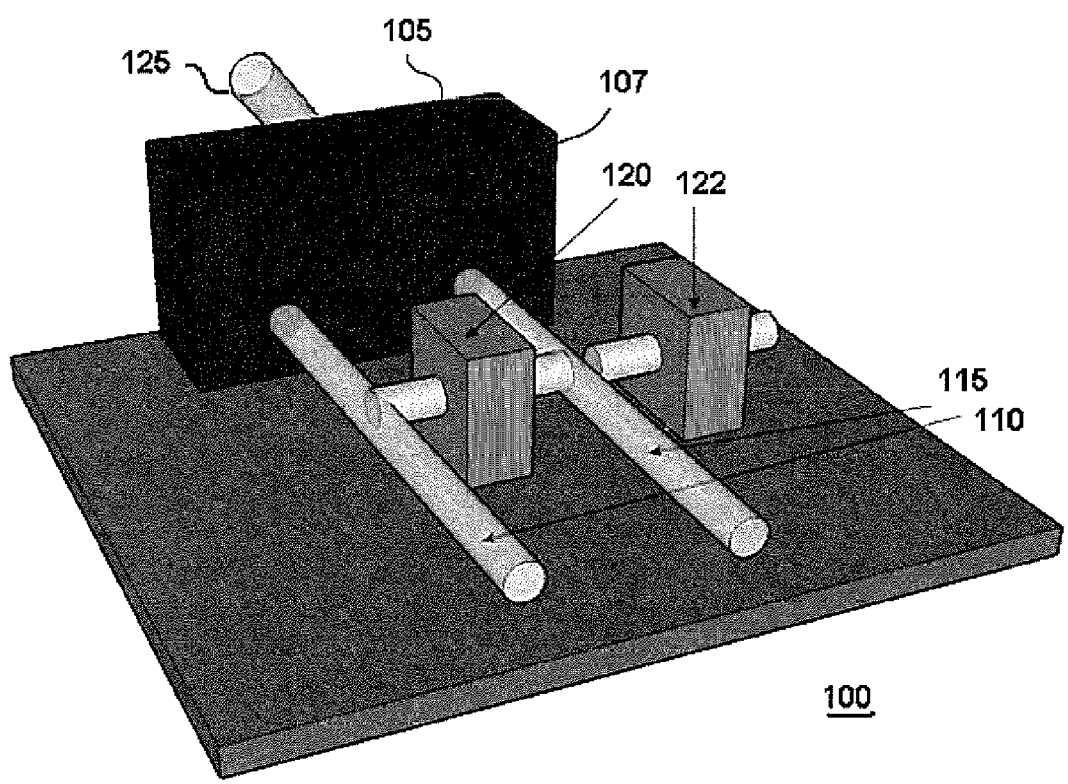
FIG. 1 shows a schematic diagram of a device for measuring concentration of a paramagnetic gas as described in one embodiment.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

In one embodiment, a device 100 for measuring concentration of a paramagnetic gas is provided. The device 100 comprises a measuring cell 105 having a closed cavity 107 therein, a measurable gas conduit 110 extending into the cavity 107 for supplying a measurable gas to the measuring cell 105 and a reference gas conduit 115 extending into the cavity 107 for supplying a reference gas to the measuring cell 105.

The device 100 further comprises a first microphone 120 differentially coupled to the measurable gas conduit 110 and the reference gas conduit 115 and a second microphone 122 located at a predetermined distance from the reference gas conduit 115. The pressure detecting microphones 120 and 122 may be condenser microphones, or electret microphones, or optical microphones, appropriate types of which are also commercially available.

The reference gas comprises a gaseous mixture having a predetermined percentage of the paramagnetic gas. More particularly, in one embodiment, the reference gas comprises a gaseous mixture having about 20.9 percent of oxygen.

The measurable gas comprises a mixture of one or more non-magnetic gases and one or more paramagnetic gases. The paramagnetic gas concentration in the measurable gas is to be measured using the device 100 for measuring concentration of the paramagnetic gas shown in FIG. 1.

The device 100 further comprises an electromagnet positioned in the cavity 107. This is further explained in conjunction with FIG. 2. The electromagnet has an electric coil and a core of ferromagnetic material that has spaced opposing magnetic poles forming the air gap with a magnetic field there between. Hereby a magnetic circuit is formed. The device 100 comprises a power source for supplying either an alternating electrical current or a chopped direct electrical current to the electric coil of the electromagnet, whereupon the magnetic field in the air gap varies respectively. This kind of power source is generally known, and is not explained in detail.

The magnetic poles N and S of the electromagnet are arranged in the air gap facing each other at a distance of a minute gap. The measuring cell 105 is surrounded by a wall made of non-magnetic materials. A mixture of paramagnetic gases and non-magnetic gases is introduced into the reference gas conduit 115. The measurable gas conduit 110 is provided on one magnetic pole N and the reference gas conduit 115 is provided on the other magnetic pole S.

Then, if the gaseous mixture containing a paramagnetic gas is introduced into the measuring cell 105 as the gas to be measured (measurable gas), an electric current is passed through the electromagnetic coil alternatively. Consequently, strong magnetic fields are alternatively generated in the space between the magnetic poles. As a result, surface-pressure is generated in proportion to the difference between the magnetizing coefficients of the gas to be measured and that of the reference gas alternatively in the minute gap between the magnetic poles.

The surface pressure generated on a boundary surface between the reference gas and the measurable gas depends on the magnetizing coefficients of the gases and the strength of the magnetic field. Accordingly, if the strength of the magnetic field and any one of the magnetizing coefficients are held constant, the magnetizing coefficient of another gas can be determined from the variation of the surface-pressure. Then the content of a paramagnetic gas, such as oxygen, in the gas to be measured can be determined from the magnetizing coefficient. Accordingly, such alternatively generated surface pressures are transmitted to the first microphone 120 through the gas conduits 110 and 115. The first microphone 120 is configured for sensing differential gas pressures in the measurable gas conduit 110 and the reference gas conduit 115, and outputting an electrical pressure signal indicating the same.

The device 100 for measuring concentration may further comprise an exit conduit 125 for removing gases from the cavity 107. The exit conduit 125 is configured for communicating with the air gap for removing the intermixed measurable and reference gases from the air gap.

In one embodiment, the paramagnetic gas comprises oxygen. The paramagnetic measurement principle is suitable for oxygen measurement as oxygen has paramagnetic properties. The magnetic susceptibility of oxygen is comparatively large, i.e. 200 times larger than e.g. the susceptibility of $N_2O$. Thus, a measuring of the susceptibility of measurable gas indicates almost exclusively the oxygen concentration.

The measurement of surface pressure resulting from oxygen concentration may be affected by mainly two types of interferences. Mechanical interferences resulting from mechanical shocks and vibrations and pneumatic interferences resulting from, for example, sudden pressure fluctuations occurring during the respiratory activity of a patient when the device 100 is coupled to a respirator for measuring oxygen content of the respiration gas. Such interferences are added to the gas signal during the process of obtaining measurements from the first microphone 120 and the second microphone 122.

The first microphone 120 provides a first signal comprising at least one mechanical signal and at least one gas signal. The gas signal represents an electrical signal indicating the surface-pressure resulting from variations in the paramagnetic gas concentration. The second microphone 122 provides a second signal, the second signal comprising at least one mechanical signal. The mechanical signal represents an electrical signal resulting from mechanical interferences that include mechanical shocks and vibrations.

The first microphone 120, which is located differentially between the measurable gas conduit 110 and the reference gas conduit 115, is connected such that pneumatic interference in the measurable gas conduit 110 and pneumatic interference in the reference gas conduit 115 cancel one another.

The second microphone 122 is not connected pneumatically to the reference gas conduit 115. The second microphone 122 is connected such that it senses only the mechanical signal and not the gas signal or the pneumatic interference. Further, the mechanical connection is made in a way that the second microphone 122 senses the mechanical interference in approximately the same way as the first microphone 120. This way the mechanical interference affects both the microphones 120 and 122 similarly, whereupon their electrical outputs correspond to each other.

The phase and magnitude of the mechanical interference can be adjusted to be the same in the first microphone 120 and the second microphone 122 by using a controlled mechanical interference. The adjustment when carried out ensures that the mechanical interferences affecting the first microphone 120 and the second microphone 122 are cancelled out. The amplifications shall be matched properly to attain the best possible elimination of error signals caused by mechanical affects.

Figure 2:
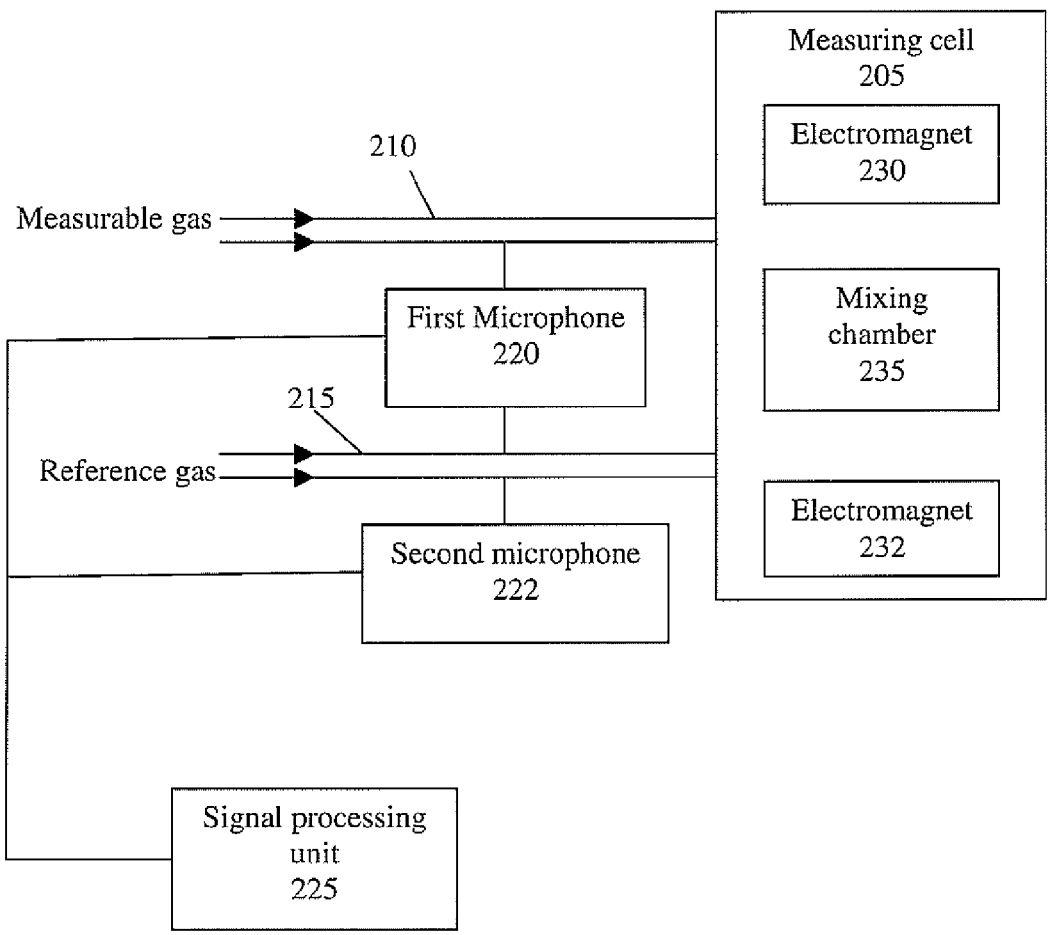
FIG. 2 shows a block diagram of a paramagnetic gas analyzer as described in one embodiment.

In another embodiment, a paramagnetic gas analyzer 200 is provided, as shown in FIG. 2. The paramagnetic gas analyzer 200 comprises a measuring cell 205 containing the reference gas and the measurable gas, a measurable gas conduit 210 for supplying the measurable gas to the measuring cell 205, a reference gas conduit 215 for supplying the reference gas to the measuring cell 205, a first microphone 220 differentially coupled between the measurable gas conduit 210 and the reference gas conduit 215, a second microphone 222 located at a predetermined distance from the reference gas conduit 215 and a signal-processing unit 225 coupled to the first microphone 220 and the second microphone 222, the signal-processing unit 225 being configured for measuring paramagnetic gas concentration of the measurable gas based on the signals from the first microphone 220 and the second microphone 222. The paramagnetic gas analyzer 200 further comprises an electromagnet comprising a pair of magnetic poles 230 and 232, each located adjacent to a mixing chamber 235 in the measuring cell 205.

The signal-processing unit 225 is connected to the microphones 220 and 222 to receive the microphone signals to form an analyzer output signal. The analyzer output signal, which is proportional to the oxygen content in the measurable gas, is a subtraction or addition of electrical output signals of pressure detecting microphones 220 and 222.

The signal-processing unit 225 comprises an electrical/electronic subtraction unit or addition unit, which have inputs that are connected to the electrical outputs of the pressure detecting microphones 220 and 222. Depending on the electronic components there can be amplifiers between the electrical outputs of the microphones 220 and 222 and the inputs of the subtraction/addition unit to amplify the signals. The subtraction/addition unit produces a subtraction or addition signal at its output for forwarding the subtraction/addition signal to other components or devices, like further calculations and/or display. This subtraction/addition signal forms the analyzer output signal and is the result of subtraction between or addition of signals from the microphones 220 and 222. In practice the mentioned subtraction or addition is performed in a computer or in some other digital processing unit, whereupon the signals are at first gone through generally known analog-to-digital conversions, like A/D converters.

Figure 3:
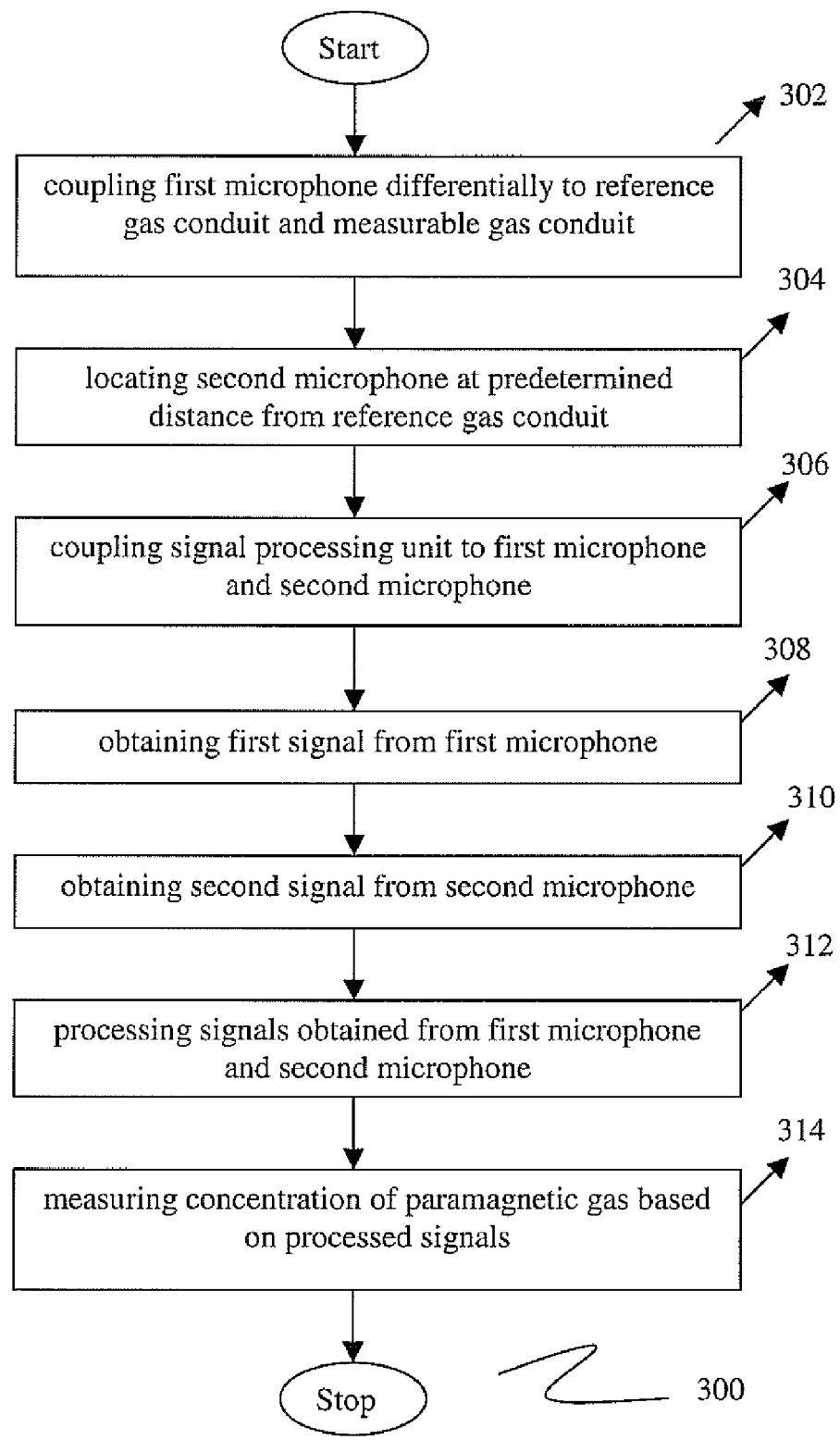
FIG. 3 shows a flow diagram depicting a method of measuring concentration of a paramagnetic gas as described in one embodiment.

In another embodiment, as shown in FIG. 3, a method 300 of measuring concentration of a paramagnetic gas is provided. The method 300 comprises steps of coupling the first microphone 220 differentially to the measurable gas conduit 210 and the reference gas conduit 215 at step 302, locating the second microphone 222 at a predetermined distance from the reference gas conduit 215 at step 304, coupling the signal-processing unit 225 to the first microphone 220 and the second microphone 222 at step 306, obtaining at least one first signal from the first microphone 220 at step 308, obtaining at least one second signal from the second microphone 222 at step 310, processing the signals obtained from the first microphone 220 and the second microphone 222 at step 312 and measuring concentration of the paramagnetic gas based on the processed signals at step 314.

The concentration of paramagnetic gas in the gas to be measured is detected from a surface-pressure generated within the measuring cell 205 between the gas to be measured and the reference gas, the surface-pressure being due to a difference of magnetizing coefficients of the gas to be measured and the reference gas passing through magnetic fields generated alternatively between the magnetic pole pieces 230 and 232 located within the measuring cell 205.

This magnetic pressure difference, proportional to the oxygen content difference between the gases in the measurable and reference gas conduits 210 and 215, is measured using the first pressure-detecting microphone 220. If the pneumatic paths of the measurable and reference gas conduits 210 and 215 are identical, a pneumatic signal representing the pneumatic interference, has equal amplitude and phase in both the measurable gas conduit 210 and the reference gas conduit 215. The value of the concentration of the paramagnetic gas, for example the oxygen content, in the measured gas mixture is thus an accurate differential signal whereas the interference caused by the pneumatic signals is automatically eliminated.

The method further comprises detecting mechanical interference in the paramagnetic gas analyzer 200 using the second microphone 222. The second microphone 222 is configured such that the second microphone 222 measures only the mechanical interference. This way, the magnitude and phase of the mechanical interference can be measured in real time.

The step of processing the signals comprises subtracting the signals obtained from the first microphone 220 and the second microphone 222. The gas signal free of the mechanical interference can be obtained by subtracting the second signal obtained from the second microphone 222 from the first signal obtained from the first microphone 220.

By eliminating these two sources of interference, namely the pneumatic interference and the mechanical interference, the obtained gas signal is free of significant noises.

Figure 4:
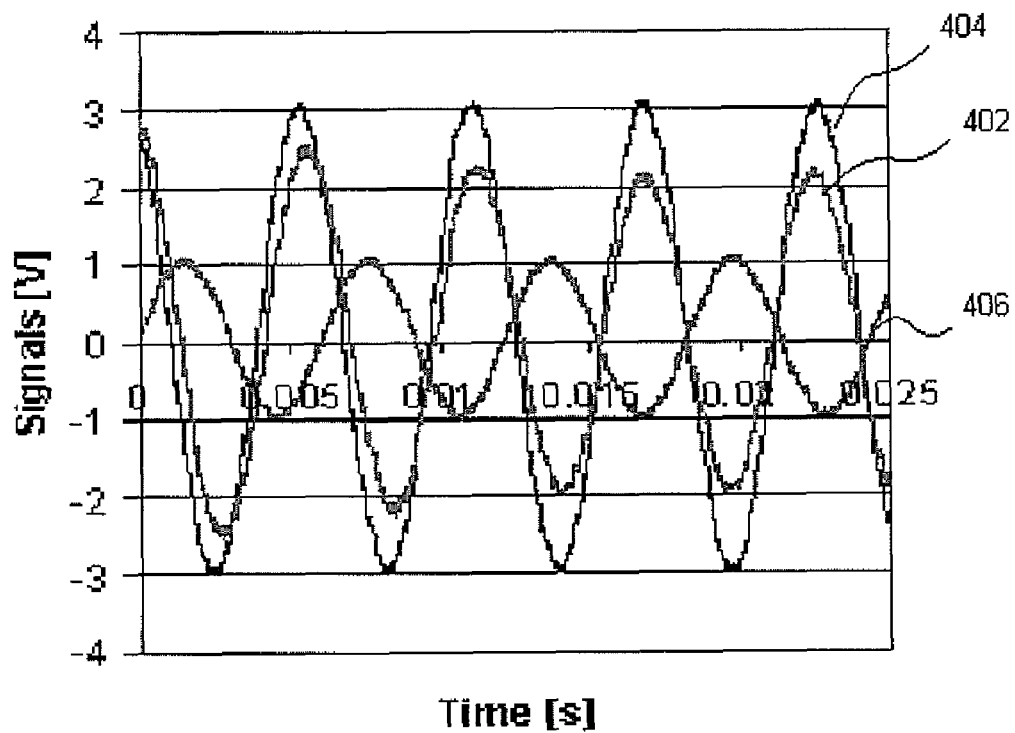
FIG. 4 and FIG. 5 show calibrated electrical signals from the first microphone and the second microphone and an analyzer output signal as described in one embodiment.
Figure 5:
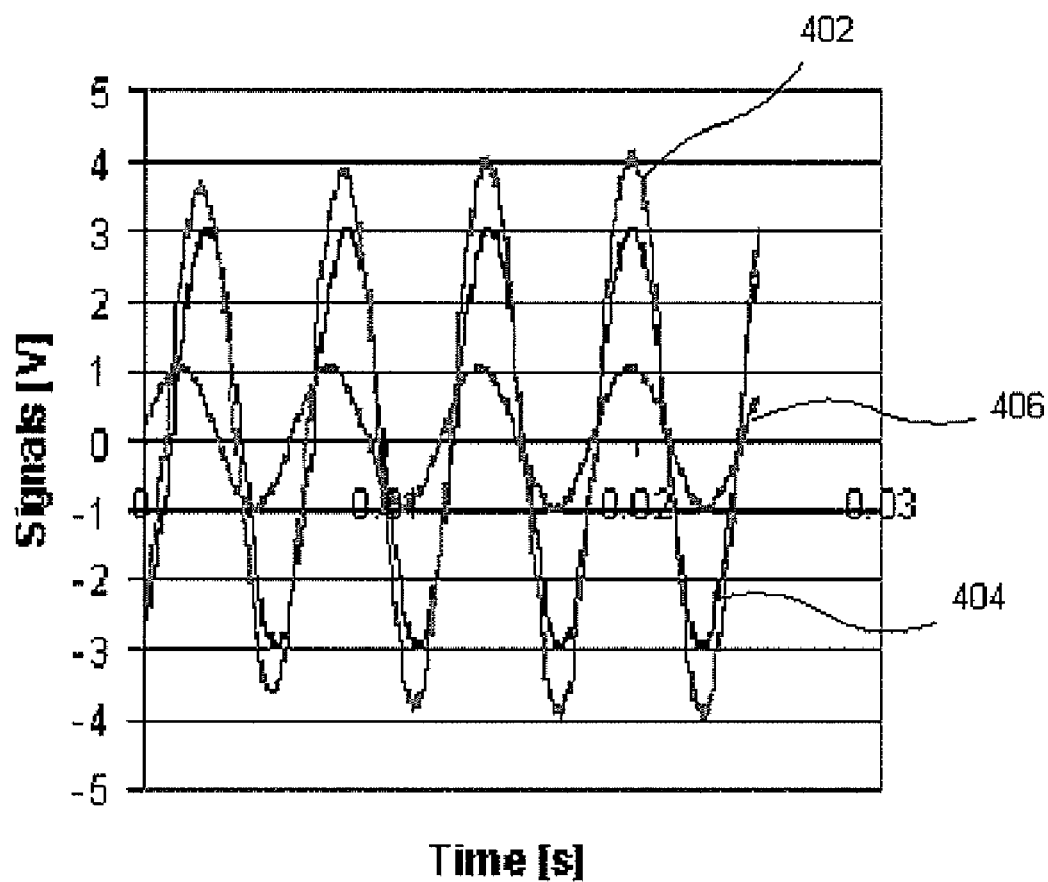

FIG. 4 and FIG. 5 show exemplary diagrams of the signals measured by the first microphone 220 and the second microphone 222. Signal 402 represents the first signal obtained from the first microphone 220 and signal 404 represents the second signal obtained from the second microphone 222. Further, signal 406 represents the gas signal obtained as the analyzer output signal. In this exemplary embodiment, the first microphone 220 measures a mechanical interference at frequency 174 Hz and a gas signal at frequency 164 Hz. The second microphone 222 is positioned to measure only the mechanical interference at frequency 174 Hz. The gas signal 406 is obtained by subtracting the two signals 402 and 404. The gas signal 406 thus obtained is substantially free from the mechanical interference and the pneumatic interference.

In FIG. 4 the mechanical signal is approximately in the opposite phase as the gas signal and in FIG. 5 the mechanical signal and the gas signal are approximately in the same phase.

There are almost unlimited applications for the measurement of proportions of gases in a gaseous mixture. A particular example is rapid measurement of oxygen and carbon dioxide in the presence of nitrogen for evaluation of metabolic activity in humans or other organisms by indirect calorimetry. Other uses include general laboratory use, monitoring of combustion gases, and monitoring of green houses gases.

The second microphone used for measuring mechanical interference and thereby generate the second signal can also be used to detect mechanical interference and its quantity.

The performance of the analyzer under pneumatic and mechanical stress is better than performance of the prior art solutions.

The paramagnetic gas analyzer described herein is economical as the cost of the analyzer is approximately the same as is the cost of the prior art solutions.

In various embodiments of the invention, a paramagnetic gas analyzer for a patient monitoring system and a patient monitoring system using a paramagnetic gas analyzer are described. However, the embodiments are not limited and may be implemented in connection with different applications. The application of the invention can be extended to other areas, for example anesthetic devices. The invention provides a broad concept of using a paramagnetic gas analyzer for measuring concentration of a paramagnetic gas, which can be adapted in a similar monitoring or measuring systems. The design can be carried further and implemented in various forms and specifications.

This written description uses examples to describe the subject matter herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device for measuring concentration of a paramagnetic gas, the device comprising:
    a measuring cell having a closed cavity therein;
    a measurable gas conduit extending into the cavity for supplying a measurable gas to the measuring cell;
    a reference gas conduit extending into the cavity for supplying a reference gas to the measuring cell;
    a first microphone differentially coupled to the measurable gas conduit and the reference gas conduit;
    a second microphone located at a predetermined distance from the reference gas conduit; and
    an electromagnet positioned in the cavity, the electromagnet having a core with spaced opposing magnetic poles forming an air gap therebetween, the electromagnet being energizable for establishing a magnetic field in the air gap, at least one of the magnetic poles having passages extending therethrough and opening into the air gap, the passages being connected to the gas conduits for supplying measurable and reference gases to the air gap.

2. The device of claim 1, further comprising an exit conduit for removing gases from the cavity.

3. The device of claim 1, wherein the paramagnetic gas comprises oxygen.

4. The device of claim 1, wherein the first microphone is connected such that pneumatic interference in the measurable gas conduit and pneumatic interference in the reference gas conduit cancel one another.

5. The device of claim 1, wherein the first microphone provides a first signal, the first signal comprising at least one mechanical signal and at least one gas signal, the mechanical signal representing mechanical interferences and the gas signal representing paramagnetic gas content of the measurable gas.

6. A paramagnetic gas analyzer comprising:
    a measuring cell containing a reference gas and a measurable gas, the measurable gas comprising a measurable concentration of the paramagnetic gas and the reference gas comprising a predetermined concentration of the paramagnetic gas;
    a reference gas conduit for supplying the reference gas to the measuring cell;
    a measurable gas conduit for supplying the measurable gas to the measuring cell;
    a first microphone differentially coupled between the reference gas conduit and the measurable gas conduit, the first microphone being configured for providing a first signal, the first signal comprising at least one mechanical signal and at least one gas signal;
    a second microphone located at a predetermined distance from the reference gas conduit, the second microphone being configured for providing at least one mechanical signal;
    a signal processing unit coupled to the first microphone and the second microphone, the signal processing unit being configured for measuring paramagnetic gas concentration of the measurable gas based on the signals from the first microphone and the second microphone; and
    an electromagnet positioned in the cavity, the electromagnet having a core with spaced opposing magnetic poles forming an air gap therebetween, the electromagnet being energizable for establishing a magnetic field in the air gap, at least one of the magnetic poles having passages extending therethrough and opening into the air gap, the passages being connected to the gas conduits for supplying measurable and reference gases to the air gap.

7. The paramagnetic gas analyzer of claim 6, wherein the second microphone is not connected pneumatically to the reference gas conduit.

8. The paramagnetic gas analyzer of claim 6, wherein the mechanical signal represents an electrical signal resulting from mechanical interferences.

9. The paramagnetic gas analyzer of claim 6, wherein the gas signal represents an electrical signal indicating surface-pressure resulting from variations in the paramagnetic gas concentration.

10. The paramagnetic gas analyzer of claim 6, wherein the first microphone is connected such that pneumatic interference in the measurable gas conduit and pneumatic interference in the reference gas conduit cancel one another.

11. The paramagnetic gas analyzer of claim 6, wherein the paramagnetic gas comprises oxygen.

12. A method of measuring concentration of a paramagnetic gas, the method comprising:
    coupling a first microphone differentially to a reference gas conduit and a measurable gas conduit, the reference gas conduit configured for supplying a reference gas and the measurable gas conduit configured for supplying a measurable gas, the reference gas comprising a predetermined concentration of the paramagnetic gas and the measurable gas comprising a measurable concentration of the paramagnetic gas;

locating a second microphone at a predetermined distance from the reference gas conduit;

coupling a signal processing unit to the first microphone and the second microphone;

positioning an electromagnet in the cavity, the electromagnet having a core with spaced opposing magnetic poles forming an air gap therebetween, wherein at least one of the magnetic poles has passages extending therethrough and opening into the air gap, the passages being connected to the gas conduits for supplying measurable and reference gases to the air gap;

energizing the electromagnet to establish a magnetic field in the air gap;

obtaining a first signal from the first microphone, the first signal comprising at least one mechanical signal and at least one gas signal; obtaining a second signal from the second microphone, the second signal comprising at least one mechanical signal;

processing the signals obtained from the first microphone and the second microphone; and measuring concentration of the paramagnetic gas based on the processed signals.

13. The method of claim 12, wherein the mechanical signal represents an electrical signal resulting from mechanical interferences and the gas signal represents an electrical signal indicating surface-pressure resulting from variations in the paramagnetic gas concentration.

14. The method of claim 12, further comprising detecting mechanical interferences in a paramagnetic gas analyzer using the second microphone.

15. The method of claim 14, wherein the step of processing the signals comprises subtracting the signals from the first microphone and the second microphone.

16. The method of claim 12, wherein the reference gas comprises a gaseous mixture having a predetermined percentage of the paramagnetic gas.

17. The method of claim 16, wherein the reference gas comprises a gaseous mixture having about 20.9 percent of oxygen.

18. The method of claim 12, wherein the measurable gas comprises a mixture of one or more non-magnetic gases and one or more paramagnetic gases.

19. The method of claim 18, wherein the paramagnetic gas comprises oxygen.

* * * * *